US012788311B2

(12) United States Patent
Maier et al.

(10) Patent No.: US 12,788,311 B2
(45) Date of Patent: Nov. 10, 2026

(54) METHOD AND DEVICES FOR POINT-OF-CARE APPLICATIONS

(71) Applicant: Roche Diagnostics Operations, Inc., Indianapolis, IN (US)

(72) Inventors: Michael Maier, Mannheim (DE); Ulrich Porsch, Weinheim (DE); Ralf Schmitz, Weinheim (DE)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 587 days.

(21) Appl. No.: 18/311,631

(22) Filed: May 3, 2023

(65) Prior Publication Data

US 2023/0270374 A1 Aug. 31, 2023

Related U.S. Application Data

(63) Continuation of application No. PCT/EP2021/082419, filed on Nov. 22, 2021.

(30) Foreign Application Priority Data

Nov. 23, 2020 (EP) .................................... 20209226

(51) Int. Cl.
*A61B 5/00* (2006.01)
*A61B 5/0205* (2006.01)
(Continued)

(52) U.S. Cl.
CPC ............ *A61B 5/445* (2013.01); *A61B 5/0205* (2013.01); *A61B 5/6898* (2013.01); *G16H 30/20* (2018.01);
(Continued)

(58) Field of Classification Search
CPC ..... A61B 5/445; A61B 5/0205; A61B 5/6898; A61B 5/1455; A61B 2562/0295; G16H 30/20
See application file for complete search history.

(56) References Cited

U.S. PATENT DOCUMENTS 10,117,617 B2 * 11/2018 Cantu ...................... A61B 5/72
10,595,756 B2 * 3/2020 Taub .................. A61B 5/14532
(Continued)

FOREIGN PATENT DOCUMENTS

EP 1976434 B1 1/2016
JP 2014509874 4/2014
(Continued)

OTHER PUBLICATIONS

Aggidis, Elsevier, 2015, pp. 243-262.*
(Continued)

*Primary Examiner* — Michael I Ezewoko
(74) *Attorney, Agent, or Firm* — Woodard, Emhardt, Henry, Reeves & Wagner, LLP

(57) ABSTRACT

A handheld diagnostic device, specifically for point-of-care applications. The handheld diagnostic device comprises at least one diagnostic measurement unit configured for performing at least one diagnostic measurement, the diagnostic measurement unit comprising at least one test element port for determining at least one diagnostic parameter of at least one patient by using at least one diagnostic test element; at least one camera configured for capturing at least one image of at least one wound of the patient; and at least one control unit, the control unit being configured for controlling the diagnostic measurement and for controlling the capturing of the image of the wound, wherein the control unit is further configured for storing at least one measurement result of the diagnostic measurement and the at least one image in at least
(Continued)

one database record of the patient. A diagnostic system and a diagnostic method are further disclosed.

17 Claims, 3 Drawing Sheets

(51) Int. Cl.
*G16H 30/20* (2018.01)
*A61B 5/1455* (2006.01)

(52) U.S. Cl.
CPC ..... *A61B 5/1455* (2013.01); *A61B 2562/0295* (2013.01)

(56) References Cited

U.S. PATENT DOCUMENTS

| | | | |
|---|---|---|---|
| 10,783,632 | B2 | 9/2020 | Fan et al. |
| 2013/0335545 | A1 | 12/2013 | Darling |
| 2016/0206205 | A1 | 7/2016 | Wu et al. |
| 2020/0029887 | A1 | 1/2020 | Buchanan et al. |
| 2020/0229765 | A1 | 7/2020 | Peabody |

FOREIGN PATENT DOCUMENTS

| | | |
|---|---|---|
| JP | 2017504370 | 2/2017 |
| WO | WO 2005078439 | 8/2005 |

OTHER PUBLICATIONS

Friesen, Marcia R. et al., A mHealth Application for Chronic Wound Care: Findings of a User Trial, International Journal of Environmental Research and Public Health, 2013, pp. 6199-6214, vol. 10.
International Search Report issued Feb. 18, 2022, in Application No. PCT/EP2021/082419, 3 pp.
Wang, Lei et al., Smartphone-Based Wound Assessment System for Patients With Diabetes, IEEE Transactions on Biomedical Engineering, 2015, pp. 477-488, vol. 62, No. 2.

* cited by examiner

METHOD AND DEVICES FOR POINT-OF-CARE APPLICATIONS

CROSS-REFERENCE TO RELATED APPLICATIONS

This application is a continuation of International Patent Application No. PCT/EP2021/082419, filed 22 Nov. 2021, which claims priority to European Patent Application No. 20209226.8, filed 23 Nov. 2020, the disclosures of which are hereby incorporated by reference in their entirety

TECHNICAL FIELD

The present disclosure refers to a handheld diagnostic device and a diagnostic system, specifically for point-of-care applications. The disclosure further relates to a diagnostic method and to computer programs and computer-readable storage media. The device, system and method specifically may be used in medical diagnostics and treatment, specifically for point-of-care applications, such as in hospitals or other healthcare facilities.

In the field of medical diagnostics, in many cases, one or more diagnostic parameters of a patient are measured. As an example, one or more diagnostic parameters have to be detected in samples of a bodily fluid, such as blood, interstitial fluid, urine, *salvia*, or other types of body fluids. Examples of diagnostic parameters to be detected are glucose, triglycerides, lactate, cholesterol, coagulation parameters or other types of diagnostic parameters typically present in these body fluids. According to the concentration, the presence and/or the temporal development of the diagnostic parameter, an appropriate treatment may be chosen, if necessary. Without narrowing the scope, the disclosure specifically may be described with respect to blood glucose measurements. It shall be noted, however, that the present disclosure may also be used for other types of diagnostic measurements using diagnostic test elements.

In case the patient may be suffering from a disease, such as diabetes, a constant monitoring of the blood glucose value, for example by blood glucose measurements using diagnostic test elements and handheld diagnostic devices, may be indicated. Further, an additional consequence specifically of diabetes, but also of other diseases, may be a significantly decrease in wound healing capacity of the patients. Therefore, looking after wounds in those patients may require specially trained nursing personal, often also called "wound managers". The workflow that may need to be followed for this is captured in paper-based process descriptions and/or paper-based progress descriptions, which may need to be complemented by taking pictures of the wound(s) of these patients.

Generally, methods and devices known to the skilled person make use of wound management applications implemented on standard mobile devices, such as smartphones or tablet computers. With regard to these wound management applications, reference may be made, e.g., to M. R. Friesen, C. Hamel and R. D. McLeod, *A mHealth Application for Chronic Wound Care: Findings of a User Trial*, Int. J. Environ. Res. Public Health Vol. 10(11), 2013, 6199-6214. Here, a user trial of a mHealth application for pressure ulcer (bedsore) documentation is reported. A software application is developed for Android smartphones and tablets and is trialed in a personal care home. The software application provides an electronic medical record for chronic wounds, replacing nurses' paper-based charting and is positioned for integration with facility's larger eHealth framework.

L. Wang, P. C. Pedersen, D. M. Strong, B. Tulu, E. Agu and R. Ignotz, *Smartphone-Based Wound Assessment System for Patients With Diabetes*, IEEE Trans. Biomed. Eng. Vol. 62(2), 2015, 477-488, describe a wound image analysis system implemented solely on the Android smartphone. The wound image is captured by the camera on the smartphone with the assistance of an image capture box. After that, the smartphone performs wound segmentation by applying the accelerated mean-shift algorithm. Specifically, the outline of the foot is determined based on skin color, and the wound boundary is found using a simple connected region detection method. Within the wound boundary, the healing status is next assessed based on red-yellow-black color evaluation model. Moreover, the healing status is quantitatively assessed, based on trend analysis of time records for a given patient.

Despite the advantages achieved by the known methods and devices, specifically by using wound management applications on general mobile devices, several technical challenges remain. Thus, the wound management process typically is a paper-based process and merging the process reports and the pictures, which are typically taken with non-compliant personal mobile devices, into an electronic health record is a manual and hence error-prone process which also bears the risk to be forgotten. Further, using a wound management application on a mobile device typically requires either the usage of a personal mobile device or at least an additional mobile device by healthcare professionals. A major technical challenge relies therefore on the fact that using a personal and/or an additional mobile device in the field of medical diagnostics leads to issues with information technology security and compliance. Further, a personal and/or an additional mobile device typically lacks physical robustness. Last but not least, hygienic requirements in the field of healthcare, like cleaning and disinfection of the used devices, often are incompatible with the use of personal mobile devices.

It is therefore desirable to provide methods and devices which address the above-mentioned technical challenges of using personal and/or additional mobile devices in the field of medical diagnostics.

SUMMARY

Although the embodiments of the present disclosure are not limited to specific advantages or functionality, it is noted that in accordance with the present disclosure a handheld diagnostic device, a diagnostic system, a diagnostic method, computer programs and computer-readable storage media are provided which allow for a user-friendly point-of-care application of diagnostic measurements and wound management processes with a high level of security in information technology and a high hygienic standard.

In accordance with one embodiment of the present disclosure, a handheld diagnostic device is provided comprising: at least one diagnostic measurement unit configured for performing at least one diagnostic measurement, the diagnostic measurement unit comprising at least one test element port for determining at least one diagnostic parameter of at least one patient by using at least one diagnostic test element; at least one camera configured for capturing at least one image of at least one wound of the patient; and at least one control unit, the control unit being configured for controlling the diagnostic measurement and for controlling the capturing of the image of the wound, wherein the control unit is further configured for storing at least one measurement result of the diagnostic measurement and the at least one image in at least one database record of the patient.

In accordance with another embodiment of the present disclosure, a diagnostic system is provided comprising: at least one handheld diagnostic device according to an embodiment of the present disclosure; and at least one server device, the server device being configured for retrieving at least one measurement result of the diagnostic measurement and/or the at least one image of the at least one wound of the patient from the handheld diagnostic device.

In accordance with yet another embodiment of the present disclosure, a diagnostic method is provided, the diagnostic method comprising using at least one handheld diagnostic device according to an embodiment of the present disclosure referring to a handheld diagnostic device, the method comprising: performing at least one diagnostic measurement, the diagnostic measurement comprising using the diagnostic measurement unit and at least one diagnostic test element for determining at least one diagnostic parameter of at least one patient; capturing at least one image of at least one wound of the patient by using the camera of the handheld diagnostic device; and storing at least one measurement result of the diagnostic measurement and the at least one image in at least one database record of the patient.

In accordance with yet still another embodiment of the present disclosure, a computer program is provided comprising instructions which, when the program is executed by the control unit of the handheld diagnostic device according to an embodiment of the present disclosure referring to a handheld diagnostic device, cause the control unit to: prompt a user to carry out a diagnostic measurement by using the diagnostic measurement unit and the diagnostic test element; prompt the user to capture the at least one image of the at least one wound of the patient by using the camera; and store at least one measurement result of the diagnostic measurement and the at least one image in the at least one database record of the patient.

In accordance with still yet another embodiment of the present disclosure, a computer-readable storage medium is provided comprising instructions which, when executed by the control unit of the handheld diagnostic device according to an embodiment of the present disclosure referring to a handheld diagnostic device, cause the control unit to: prompt a user to carry out a diagnostic measurement by using the diagnostic measurement unit and the diagnostic test element; prompt the user to capture the at least one image of the at least one wound of the patient by using the camera; and store at least one measurement result of the diagnostic measurement and the at least one image in the at least one database record of the patient.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present description can be best understood when read in conjunction with the following drawings, where like structure is indicated with like reference numerals and in which.

Figure 1:
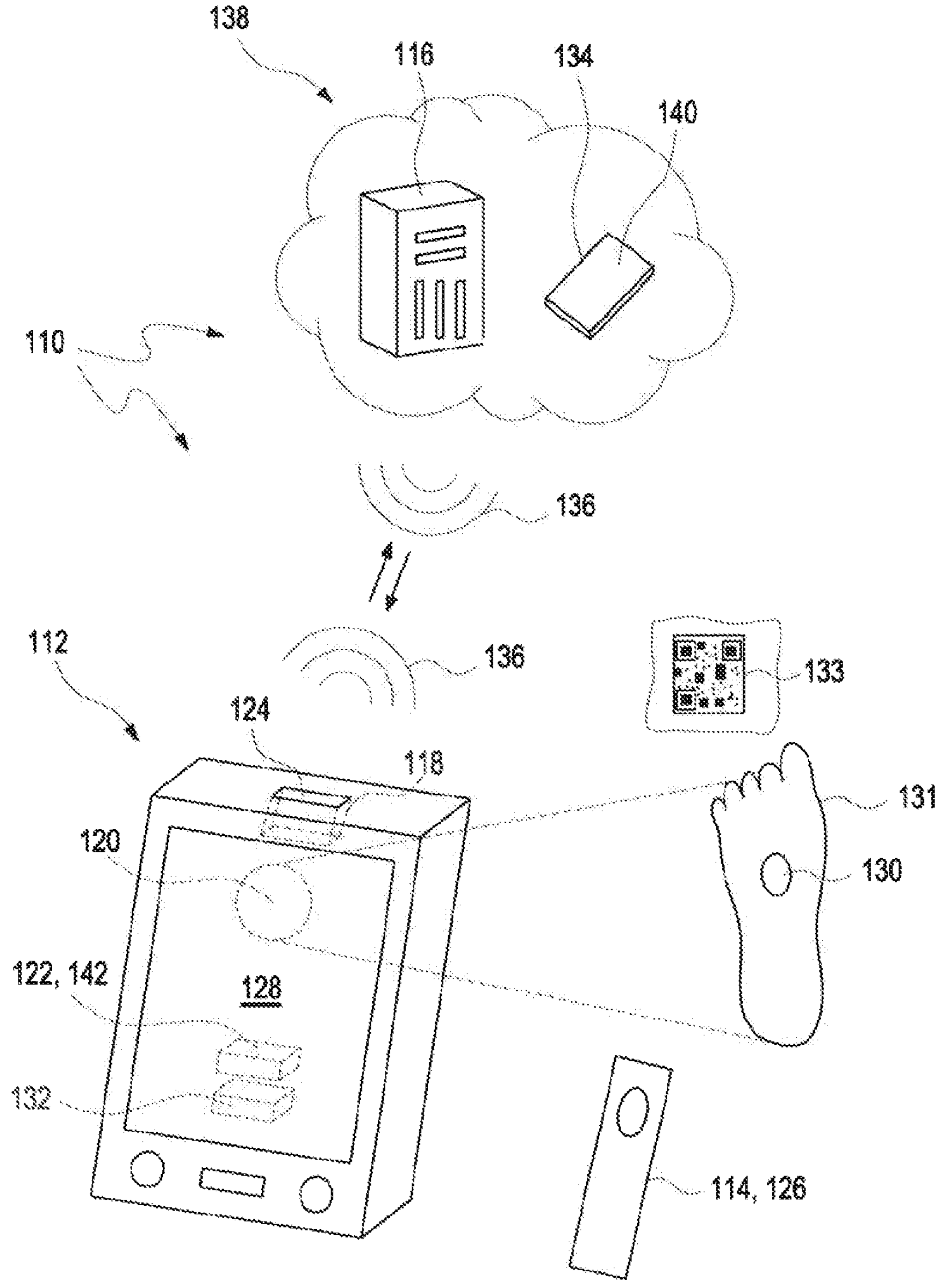
FIG. 1 shows embodiments of a diagnostic system, a handheld diagnostic device and a diagnostic test element in a schematic view in accordance with an embodiment of the present disclosure.

Skilled artisans appreciate that elements in the figures are illustrated for simplicity and clarity and have not been drawn to scale. For example, dimensions of some of the elements in the figures may be exaggerated relative to other elements to help improve understanding of the embodiment(s) of the present disclosure.

DETAILED DESCRIPTION

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "typically", "more typically", "particularly", "more particularly", "specifically", "more specifically" or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in such way with other optional or non-optional features of the disclosure.

In a first aspect of the disclosure, a handheld diagnostic device is disclosed, specifically for point-of-care applications. The handheld diagnostic device comprises:

a. at least one diagnostic measurement unit configured for performing at least one diagnostic measurement, the diagnostic measurement unit comprising at least one test element port for determining at least one diagnostic parameter of at least one patient by using at least one diagnostic test element;

b. at least one camera configured for capturing at least one image of at least one wound of the patient, specifically of the same patient as in a.; and c. at least one control unit, the control unit being configured for controlling the diagnostic measurement and for controlling the capturing of the image of the wound, wherein the control unit is further configured for storing at least one measurement result of the diagnostic measurement and the at least one image in at least one database record of the patient.

The term "handheld diagnostic device" as used herein is a broad term and is to be given its ordinary and customary meaning to a person of ordinary skill in the art and is not to be limited to a special or customized meaning. The term specifically may refer, without limitation, to an arbitrary, portable device configured for conducting at least one diagnostic examination of a patient and/or of a biological sample. The handheld diagnostic device specifically may be configured, by its dimensions and/or its weight, for being carried by a user with a single hand. Thus, as an example, a volume of the handheld diagnostic device may not exceed 0.001 $m^3$, as will be outlined in further detail below, and/or the weight of the handheld diagnostic device may not exceed 1 kg.

The handheld diagnostic device comprises at least one diagnostic measurement unit, at least one camera and at least one control unit. Specifically, the handheld diagnostic device may be configured for performing at least one diagnostic measurement, such as for determining at least one diagnostic parameter of at least one patient, e.g., for qualitatively and/or quantitatively determining the concentration of at least one analyte in a sample, such as a sample of a bodily fluid. Thus, the handheld diagnostic device specifically may be or may comprise at least one measurement device for measuring the at least one diagnostic parameter, such as a blood glucose measurement device and/or such as a coagulation measurement device. Other options are feasible.

Further, the handheld diagnostic device may be configured for performing at least one wound management process, such as for capturing at least one image of a wound of at least one patient and for further processing of that image, such as for image processing, in order to for example determine the lateral extension of the wound. Thus, the handheld diagnostic device may be a combined handheld diagnostic device configured both for performing at least one diagnostic measurement and for assisting a user in a wound management of a patient. The handheld diagnostic device may further comprise a display and/or a screen, specifically a touchscreen, which is configured for interacting with a user of the handheld diagnostic device. For example, the display of the handheld diagnostic device may be configured for displaying the result of the diagnostics measurement and/or for displaying captured images. The handheld diagnostic device may be configured for point-of-care applications such as by fulfilling standards for point-of-care applications and/or hospitals.

The term "point-of-care applications" as used herein is a broad term and is to be given its ordinary and customary meaning to a person of ordinary skill in the art and is not to be limited to a special or customized meaning. The term specifically may refer, without limitation, to an application in a professional healthcare facility, wherein the application is performed by a professional healthcare provider, specifically at or near to the patient. For example, a diagnostic examination of a patient using the handheld diagnostic device may take place in a hospital or in a medical office. Other options are also feasible.

The term "diagnostic measurement unit" as used herein is a broad term and is to be given its ordinary and customary meaning to a person of ordinary skill in the art and is not to be limited to a special or customized meaning. The term specifically may refer, without limitation, to an arbitrary device configured for determining the presence, the concentration and/or the temporal development of at least one diagnostic parameter of at least one patient. Specifically, the diagnostic measurement unit may be configured for performing a diagnostic measurement using at least one diagnostic test element. Thus, the diagnostic measurement unit may comprise at least one test element port for receiving at least one diagnostic test element. As an example, the diagnostic measurement unit may comprise a diagnostic measurement unit having at least one device for electrochemical testing and/or optical testing of a sample, such as by using at least one electrochemical test element and/or at least one optical test element for testing a biological sample, such as a test strip or a test cartridge.

Consequently, the term "performing at least one diagnostic measurement" as used herein is a broad term and is to be given its ordinary and customary meaning to a person of ordinary skill in the art and is not to be limited to a special or customized meaning. The term specifically may refer, without limitation, to a process of generating at least one representative result or a plurality of representative results indicating at least one medical parameter and/or at least one diagnostic parameter, such as at least one parameter of a sample, e.g., one or more of the concentration of at least one analyte in the sample, the presence of the at least one analyte in the sample and/or the temporal development of the diagnostic parameter in the sample, such as in a sample of a bodily fluid of the patient.

The term "diagnostic measurement", also referred to as "determining at least one diagnostic parameter", as used herein is a broad term and is to be given its ordinary and customary meaning to a person of ordinary skill in the art and is not to be limited to a special or customized meaning. The term specifically may refer, without limitation, to a quantitative and/or qualitative determination of at least one diagnostic parameter in an arbitrary sample or aliquot of bodily fluid. For example, the bodily fluid may comprise one or more of blood, blood derivatives like plasma or serum, interstitial fluid, urine, saliva or other types of body fluids and their derivatives. The result of determining a diagnostic parameter, as an example, may be a concentration of at least one analyte and/or the presence or absence of the at least one analyte and/or another value of the at least one diagnostic parameter to be determined, such as a coagulation parameter. Specifically, as an example, the diagnostic measurement may be a blood glucose measurement, thus the result of the diagnostic measurement may be for example a blood glucose concentration. As another example, the diagnostic measurement may be a coagulation measurement, thus the result of the diagnostic measurement may be a coagulation value, specifically a temporal parameter like a coagulation time or a parameter derived therefrom. In particular, a diagnostic measurement result value may be determined by the diagnostic measurement.

Consequently, the term "diagnostic measurement result value", also referred to as a "measurement result of the diagnostic measurement", as used herein, is a broad term and is to be given its ordinary and customary meaning to a person of ordinary skill in the art and is not to be limited to a special or customized meaning. The term specifically may refer, without limitation, to a numerical indication of at least one diagnostic parameter, such as a concentration of at least one analyte in a sample and/or another type of diagnostic parameter, such as a numerical indication of the coagulation value in the sample. The at least one diagnostic parameter, as an example, may be or may comprise a concentration of at least one analyte, such as at least one specific chemical compound, and/or may also comprise other parameters. As an example, one or more diagnostic parameters may be determined which take part in metabolism, such as blood glucose. Additionally or alternatively, other types of diagnostic parameters may be determined, e.g., a pH value or a coagulation value.

The term "patient" as used herein is a broad term and is to be given its ordinary and customary meaning to a person of ordinary skill in the art and is not to be limited to a special or customized meaning. The term specifically may refer, without limitation, to a person independent from the fact that the person may be in healthy condition or may suffer from one or more diseases. Specifically, a patient may be a person being examined by at least one healthcare professional. For example, the patient may be a person suffering from diabetes and/or other diseases.

The term "diagnostic test element" as used herein is a broad term and is to be given its ordinary and customary meaning to a person of ordinary skill in the art and is not to be limited to a special or customized meaning. The term specifically may refer, without limitation, to an arbitrary device which is capable of detecting the diagnostic parameter in the sample. The diagnostic test element may specifically be a strip-shaped diagnostic test element, are also referred to as a test strip. As used herein, the term "strip-shaped" refers to an element having an elongated shape and a thickness, wherein an extension of the element in a lateral dimension exceeds the thickness of the element, such as by at least a factor of 2, typically by at least a factor of 5, more typically by at least a factor of 10 and most typically by at least a factor of 20 or even at least a factor of 30. Thus, the diagnostic test element may be or may comprise at least one test strip. The diagnostic test element may further comprise at least one component or at least one reagent which changes at least one detectable property when the diagnostic parameter is present in the sample, such as a test chemical.

The term "test chemical", sometimes also referred to as "test chemistry", as used herein is a broad term and is to be given its ordinary and customary meaning to a person of ordinary skill in the art and is not to be limited to a special or customized meaning. The term specifically may refer, without limitation, to an arbitrary material or a composition of materials adapted to change at least one detectable property in the presence of the diagnostic parameter. Generally, this property may be selected from an electrochemically detectable property and/or an optically detectable property, such as a color change and/or a change in remissive properties. Specifically, the test chemical may be a highly selective test chemical, which only changes the property if the diagnostic parameter is present in the sample of the body fluid applied to the diagnostic test element, whereas no change occurs if the diagnostic parameter is not present. More typically, the degree or change of the property may be dependent on an occurrence or a concentration of the diagnostic parameter in the body fluid, in order to allow for a quantitative detection of the diagnostic parameter. If the test chemical comprises an electrochemical test chemical, the diagnostic test element may be referred to as "electrochemical test element". As another example, if the test chemistry comprises an optical test chemistry, the diagnostic test element may be referred to as "optical test element".

Further, the term "test element port" as used herein is a broad term and is to be given its ordinary and customary meaning to a person of ordinary skill in the art and is not to be limited to a special or customized meaning. The term specifically may refer, without limitation, to a device for receiving and for holding the diagnostic test element. Specifically, the test element port may be or may comprise a test element holder for at least one diagnostic test element. The diagnostic test element may be positioned in a specific position within the test element holder, such that a movement of the diagnostic test element in at least one direction may be suppressed, at least to a large extent. Thus, the measurement zone of the diagnostic test element may be located in a predetermined position relative to the measuring unit. The diagnostic test element may specifically be configured to be put reversibly into the test element port. Thus, the diagnostic test element may be removable from the test element port without further ado. Additionally or alternatively, the handheld diagnostic device may also comprise at least one test element magazine which is configured for storing a plurality of the test elements and for further moving, specifically one by one, the test elements into at least one predetermined position relative to the measuring unit, wherein, as an example, the test element protrudes from the test element port in order to allow for sample application. Still, other embodiments are feasible. For example, the test element port may be configured to receive at least one test strip. Thus, the test element port may also be referred to as "test strip port".

As outlined above, the handheld diagnostic device comprises at least one camera. The term "camera" as used herein is a broad term and is to be given its ordinary and customary meaning to a person of ordinary skill in the art and is not to be limited to a special or customized meaning. The term specifically may refer, without limitation, to a device having at least one imaging element configured for recording or capturing spatially resolved one-dimensional, two-dimensional or even three-dimensional optical data or information. As an example, the camera may comprise at least one camera chip, such as at least one CCD chip and/or at least one CMOS chip configured for recording images. As used herein, without limitation, the term "image" specifically may relate to data recorded by using a camera, such as a plurality of electronic readings from the imaging device, such as the pixels of the camera chip.

The camera, besides the at least one camera chip or imaging chip, may comprise further elements, such as one or more optical elements, e.g., one or more lenses or apertures. As an example, the camera may be a fix-focus camera, having at least one lens which is fixedly adjusted with respect to the camera. Alternatively, however, the camera may also comprise one or more variable lenses which may be adjusted, automatically or manually. The disclosure specifically shall be applicable to cameras as usually used in mobile applications such as notebook computers, tablets or, specifically, cell phones such as smartphones. Thus, specifically, the camera may be part of a mobile device, such as the handheld diagnostic device, which, besides the at least one camera, comprises one or more data processing devices such as one or more data processors. Other cameras, however, are feasible.

The camera specifically may be a color camera. Thus, such as for each pixel, color information may be provided or generated, such as color values for three colors R, G, B. A larger number of color values is also feasible, such as four color values for each pixel, for example R, G, G, B. Color cameras are generally known to the skilled person. Thus, as an example, the camera chip may consist of a plurality of three or more different color sensors each, such as color recording pixels like one pixel for red (R), one pixel for green (G) and one pixel for blue (B). For each of the pixels, such as for R, G, B, values may be recorded by the pixels, such as digital values in the range of 0 to 255, depending on the intensity of the respective color. Instead of using color triples such as R, G, B, as an example, quadruples may be used, such as R, G, G, B. The color sensitivities of the pixels may be generated by color filters or by appropriate intrinsic sensitivities of the sensor elements used in the camera pixels. These techniques are generally known to the skilled person.

The term "capturing at least one image" as used herein is a broad term and is to be given its ordinary and customary meaning to a person of ordinary skill in the art and is not to be limited to a special or customized meaning. The term specifically may refer, without limitation, to one or more of imaging, image recording, image acquisition, image capturing. The term "capturing at least one image" may comprise capturing a single image and/or a plurality of images such as a sequence of images. For example, the capturing of the image may comprise recording continuously a sequence of images such as a video or a movie. The capturing of the at least one image may be initiated by the user action or may automatically be initiated, e.g., once the presence of the at least one object within a field of view and/or within a predetermined sector of the field of view of the camera is automatically detected. These automatic image acquisition techniques are known, e.g., in the field of automatic bar-code readers, such as from automatic barcode reading apps. The capturing of the images may take place, as an example, by acquiring a stream or "live stream" of images with the camera, wherein one or more of the images, automatically or by user interaction such as pushing a button, are stored. The image acquisition may be supported by a processor of the handheld diagnostic device, and the storing of the images may take place in a data storage device of the handheld diagnostic device.

The term "wound" as used herein is a broad term and is to be given its ordinary and customary meaning to a person of ordinary skill in the art and is not to be limited to a special or customized meaning. The term specifically may refer, without limitation, to an exterior injury of the skin of the patient. Specifically, the wound may be an open wound of the skin of the patient. Further, the wound may refer to an injury that requires medical treatment, such as an acute, a chronic and/or a non-healing-wound. The wound may specifically be located on the patient's feet and/or lower legs. For example, the wound may be a non-healing ulcer on the patient's feet and lower legs caused by a disease, such as diabetes. The wound may be characterized by an extension of the wound, specifically a lateral extension, describing the lateral size of the wound. In the context of wound management processes, the term "wound" may also comprise regions of the skin of the patient that are susceptible to develop wounds in the future proliferation of a disease. The imaging of such regions before the occurrence of visible wounds may be useful as a reference value for the evaluation of a wound later on.

The term "control unit" as used herein is a broad term and is to be given its ordinary and customary meaning to a person of ordinary skill in the art and is not to be limited to a special or customized meaning. The term specifically may refer, without limitation, to an electronic device configured for controlling the functionality of the handheld diagnostic device. Specifically, the control unit may be configured for controlling the diagnostic measurement, for controlling the capturing of the image of the wound and for storing the patient data in the database record of the patient. Further, the control unit may be configured for managing the database record, specifically managing the database records for a plurality of patients. For example, the control unit may be configured for assigning the measurement result of the diagnostic measurement and the image of the wound to at least one patient's electronic health record. Consequently, the term "controlling" as used herein is a broad term and is to be given its ordinary and customary meaning to a person of ordinary skill in the art and is not to be limited to a special or customized meaning. The term specifically may refer, without limitation, to the process of one or more of performing and operating an action, such as the diagnostic measurement or the capturing of the image.

The term "database" as used herein is a broad term and is to be given its ordinary and customary meaning to a person of ordinary skill in the art and is not to be limited to a special or customized meaning. The term specifically may refer, without limitation, to an organized collection of data, generally stored and accessed electronically from a computer or computer system. The database may comprise or may be comprised by a data storage device, as will be outlined in further detail below. The data base may comprise at least one data base management system, comprising a software running on a computer or computer system, the software allowing for interaction with one or more of a user, an application or the data base itself, such as in order to capture and analyze the data contained in the data base. The database management system may further encompass facilities to administer the database. The database, containing the data, may, thus, be comprised by a data base system which, besides the data, comprises one or more associated applications. Consequently, the term "database record" as used herein is a broad term and is to be given its ordinary and customary meaning to a person of ordinary skill in the art and is not to be limited to a special or customized meaning. The term specifically may refer, without limitation, to at least one item of information stored in the database in an organized fashion. Thus, as an example, each data base entry may comprise at least one package of information, wherein a plurality of packages of information may be related or linked to each other in the database. Further, the database record may contain at least one item of information on a patient, such as the at least one measurement result of the diagnostic measurement and the at least one image. The database may comprise a plurality of database records on a plurality of patients.

Further, the database record may contain at least one item of identification information identifying the patient, the at least one image and the at least on measurement result. The database record may at least partially be stored on the handheld diagnostic device, specifically in at least one data storage device of the handheld diagnostic device. The database record may further at least partially be stored on at least one server device, specifically in a hospital information system, wherein the handheld diagnostic device may be configured for electronically communicating with the server device, specifically with the hospital information system.

The term "item of identification information" as used herein is a broad term and is to be given its ordinary and customary meaning to a person of ordinary skill in the art and is not to be limited to a special or customized meaning. The term specifically may refer, without limitation, to an arbitrary characteristic that can be used to identify a patient. For example, an item of identification information may be or may comprise personal identification information, such as a name or a date of birth of the patient, and/or an identification number of the patient, such as a number given to the patient in order to uniquely identify the patient.

The term "data storage device" as used herein is a broad term and is to be given its ordinary and customary meaning to a person of ordinary skill in the art and is not to be limited to a special or customized meaning. The term specifically may refer, without limitation, to an arbitrary memory device configured to store data. Specifically, the data storage device may be an electronic, magnetic and/or mechanic memory device. For example, the data storage device may be comprised by the handheld diagnostics device. The data storage device may further be configured to store data, specifically in an organized way, such as in a database, more specifically in at least one database record.

The term "server device" as used herein is a broad term and is to be given its ordinary and customary meaning to a person of ordinary skill in the art and is not to be limited to a special or customized meaning. The term specifically may refer, without limitation, to a device which is capable of performing one or more operations with the data to be processed. Specifically, the server device may comprise at least one processor, which may be programmed, by appropriate software, for performing one or more operations with the data to be processed. The server device may be or may comprise at least one cloud server. Further, the server device may be configured to store data, such as a database, specifically at least one database record.

The term "hospital information system" as used herein is a broad term and is to be given its ordinary and customary meaning to a person of ordinary skill in the art and is not to be limited to a special or customized meaning. The term specifically may refer, without limitation, to a system which is configured, specifically by software programming, to track, manage and store documents. Specifically, the hospital information system is based on a computer program. The hospital information system may comprise at least one data interface for exchanging one or both of data or commands with the at least one handheld diagnostic device and/or with further devices. The at least one interface may be or may comprise one of a wire-bound or a wireless interface. Thus, the hospital information system may be configured for communicating with the at least one handheld diagnostic device and/or with further devices, in order to for example exchanging the at least one item of information, the at least one image and/or the at least one measurement result of the diagnostic measurement.

As outlined above, the control unit is configured for storing the at least one measurement result and the at least one image in the at least one database record. The database record of the patient may be at least partially comprised by an electronic health record stored in the hospital information system. Thus, the control unit may be configured for assigning the measurement result and the image to the at least one patient's electronic health record.

The term "electronic health record" as used herein is a broad term and is to be given its ordinary and customary meaning to a person of ordinary skill in the art and is not to be limited to a special or customized meaning. The term specifically may refer, without limitation, to a systematic collection of electronically stored patient-related health information. For example, the electronic health record may store patient-related information, such as the name, the age and the gender of the patient, and further health information, such as present diseases and/or past diseases and/or treatments. Specifically, the health information stored in the electronic health record may be or may comprise the at least one measurement result of the at least one diagnostic measurement and the at least one image of the at least one wound of the patient. Further, the electronic health record may be configured for storing health information accurately in a protected environment and for capturing the state of health of the patient across time.

As outlined above, the handheld diagnostic device may be a portable device configured for point-of-care applications. Thus, the handheld diagnostic device may comprise at least one energy storage device for providing electrical energy to at least one of the diagnostic measurement unit, the camera and the control unit. Further, the handheld diagnostic device may be a wireless handheld diagnostic device. The handheld diagnostic device may have a volume of less than 0.001 $m^3$ and a weight of less than 1 kg. Further, the handheld diagnostic device may comprise at least one display and/or at least one user interface.

The term "energy storage device" as used herein is a broad term and is to be given its ordinary and customary meaning to a person of ordinary skill in the art and is not to be limited to a special or customized meaning. The term specifically may refer, without limitation, to an arbitrary device configured for storing electrical energy. Specifically, the energy storage device may be or may comprise a battery, more specifically a battery which is configured for multiple use. Thus, in case the energy storage device is fully or partially discharged, the energy storage device may be configured for being recharged with electrical energy.

The term "user interface" as used herein is a broad term and is to be given its ordinary and customary meaning to a person of ordinary skill in the art and is not to be limited to a special or customized meaning. The term may refer, without limitation, to a feature of the handheld diagnostic device which is configured for interacting with its environment, such as for the purpose of unidirectionally or bidirectionally exchanging information, such as for exchange of one or more of data or commands. For example, the user interface of the handheld diagnostic device may be configured to share information with a user and to receive information by the user. The user interface of the handheld diagnostic device may be a feature to interact visually with a user, such as a display, or a feature to interact acoustically with the user. The user interface, as an example, may comprise one or more of: a graphical user interface; a data interface, such as a wireless and/or a wire-bound data interface.

As outlined above, the handheld diagnostic device is configured for performing at least one diagnostic measurement. The diagnostic parameter may comprise at least one parameter selected from the group consisting of: a glucose concentration in at least one body fluid of the patient, specifically a blood glucose value; a coagulation parameter of the patient; a ketone concentration in at least one body fluid of the patient, a lactate concentration in at least one body fluid of the patient. The diagnostic parameter is determined by using the at least one diagnostic test element, wherein the diagnostic test element may comprise at least one of an electrochemical test element and/or an optical test element. The diagnostic test element may comprise at least one test strip. Therefore, the test element port comprised by the diagnostic measurement unit may comprise at least one test strip port.

Further, the handheld diagnostic device may be configured for identifying at least one of the patient or a user of the handheld diagnostic device. Thus, the handheld diagnostic device may be configured for detecting at least one identifier, the identifier identifying the patient or user, respectively. The identifier may comprise at least one identifier selected from the group consisting of: an optical identifier, specifically at least one of a bar code or a QR code; an electronic identifier, specifically an RFID tag and/or an NFC tag. Alternatively, the operator can log in via a virtual keyboard. The handheld diagnostic device may further be configured for identifying the patient or user, respectively, by using image recognition, specifically by using face recognition. The handheld diagnostic device may also comprise at least one biometric sensor configured for identifying the patient by determining at least one biometric parameter of the patient or user, respectively.

The term "user" as used herein is a broad term and is to be given its ordinary and customary meaning to a person of ordinary skill in the art and is not to be limited to a special or customized meaning. The term specifically may refer, without limitation, to a person using the handheld diagnostic device. Specifically, the user may be a healthcare professional, such as a nurse or a medical doctor or another medically trained person.

The term "identifier" as used herein is a broad term and is to be given its ordinary and customary meaning to a person of ordinary skill in the art and is not to be limited to a special or customized meaning. The term specifically may refer, without limitation, to an element or a combination of elements configured for storing one or more items of information identifying the patient and/or a user of the handheld diagnostic device, such as in a readable fashion, specifically in a machine-readable fashion. Specifically, the items of information stored in the identifier may be or may comprise at least one item of identification information. The identifier may comprise at least one of an optical identifier, an electronic identifier, a magnetic identifier or a mechanical identifier. As an example, the identifier, specifically the optical identifier, may be or may comprise at least one of a one- or two-dimensional code and/or a readable information tag, such as one or more of a barcode, a QR code or another type of code directly or indirectly attached to the patient and/or the user, such as by being applied to the patient and/or to the user via at least one of: an identity card, a badge, a bracelet, a wristband. As another example, the identifier, specifically the electronic identifier, may be or may comprise at least one RFID tag and/or an NFC tag. Further embodiments or options of the identifier will be described in detail below. The information stored in the identifier may be detected using an appropriate detection device.

Consequently, the term "detecting the identifier" as used herein is a broad term and is to be given its ordinary and customary meaning to a person of ordinary skill in the art and is not to be limited to a special or customized meaning. The term specifically may refer, without limitation, to the process of retrieving at least one item of information, such as the at least one item of information stored in the identifier, such as in an electronic format, by using an appropriate detection device. The process of detecting the identifier specifically may take place electronically.

The detection may further depend on the type of identifier. Thus, the detection may comprise an optical detecting in case the identifier comprises an optical identifier, such as a bar code and/or a QR code, e.g., by optical scanning. In case the identifier comprises an electronic identifier, such as an RFID code and/or an NFC tag, detecting the identifier may comprise an electronic detection, such as a detection by near field communication (NFC). Other options are feasible. Further, the detection device may be or may comprise at least one of a bar code reader, a QR code reader, such as a camera, or a RFID reader. Specifically, the detection device may be comprised by the handheld diagnostic device. Thus, the handheld diagnostic device may be configured for detecting the at least one identifier and thereby identifying at least one of the patient and/or user of the handheld diagnostic device.

The term "bar code" as used herein is a broad term and is to be given its ordinary and customary meaning to a person of ordinary skill in the art and is not to be limited to a special or customized meaning. The term specifically may refer, without limitation, to binary optical information, such as to a binary sequence of optical information, such as a sequence of parallel lines having different widths, the binary sequence encoding information such as a number and/or an array of numbers and/or letters. Thus, the bar code may be a sequence of single colored lines having a high contrast compared to a background. Specifically, the bar code may comprise black lines on a white background.

The term "QR code" as used herein is a broad term and is to be given its ordinary and customary meaning to a person of ordinary skill in the art and is not to be limited to a special or customized meaning. The term specifically may refer, without limitation, to a quadratic matrix of binary pixels, the matrix encoding information such as a number and/or an array of numbers and/or letters. The pixels of the quadratic matrix may have a high contrast compared to a background. Specifically, the pixels of the matrix may comprise black squares arranged on a white background. Further, the QR code may comprise an indication of orientation enabling the detection device of the QR code to align the matrix.

The term "RFID tag" as used herein is a broad term and is to be given its ordinary and customary meaning to a person of ordinary skill in the art and is not to be limited to a special or customized meaning. The term specifically may refer, without limitation, to a label configured for exchanging data information with a detection device by using radio-frequency electromagnetic radiation, such as by using the NFC standard. The RFID tag may further comprise an antenna configured to receive and to emit a radio-frequency signal and an electronic chip such as a microchip configured to store the data information. Specifically, the RFID tag may be a flexible substrate having an electronic conducting coil and optionally at least one microchip.

The term "image recognition" as used herein is a broad term and is to be given its ordinary and customary meaning to a person of ordinary skill in the art and is not to be limited to a special or customized meaning. The term specifically may refer, without limitation, to a process of recognizing or identifying one or more features in an image. Specifically, the image recognition may comprise visually identifying the patient and/or user by using at least one image of the patient or user, respectively. Specifically, the patient or user may be identified by imaging a specific characteristic of the patient or user, respectively. Thus, the process of image recognition may include taking at least one image of the patient or user using the at least one camera of the handheld diagnostic device. As used in the context of a wound management process, the image recognition specifically may comprise visually identifying a feature of the wound of the patient, such as the at least one item of diagnostic information from the image, specifically at least one color information and/or size information of the wound.

The term "face recognition" as used herein is a broad term and is to be given its ordinary and customary meaning to a person of ordinary skill in the art and is not to be limited to a special or customized meaning. The term specifically may refer, without limitation, to a process of image recognition, whereby a face of the patient or user may be used to identify the patient or user, respectively. Specifically, for identifying the patient or user by face recognition, the entire face of the patient or user, respectively, may be used. As another example, only parts of the patient's or user's face may be used for identifying the patient or user, respectively, such as at least one eye and/or at least one ear of the patient or user.

The term "biometric sensor" as used herein is a broad term and is to be given its ordinary and customary meaning to a person of ordinary skill in the art and is not to be limited to a special or customized meaning. The term specifically may refer, without limitation, to an arbitrary device, which is configured for detecting at least one biometric parameter of the patient and/or the user. Specifically, the biometric sensor may be or may comprise a camera for detecting the biometric parameter by image recognition. The biometric sensor may also be or may comprise at least one fingerprint sensor. Other options are feasible. Further, the biometric sensor may be comprised by the handheld diagnostic device. For example, the camera for detecting the at least one biometric parameter by image recognition may be the same camera configured for capturing the at least one image of the at least one wound of the patient. However, the camera for detecting the at least one biometric parameter by image recognition may also be different from said camera, such as a front camera, pointing towards the user of the handheld diagnostic device.

Consequently, the term "biometric parameter" as used herein is a broad term and is to be given its ordinary and customary meaning to a person of ordinary skill in the art and is not to be limited to a special or customized meaning. The term specifically may refer, without limitation, to a biological feature of the patient or user which is suitable for identifying the patient or user, respectively. Specifically, the biometric parameter may be or may comprise a unique biological feature of the patient or user, which may be constant in time, detectable and further inherent to every person, such as the patient or user. As an example, the biological parameter may be or may comprise at least one fingerprint of at least one finger or thumb of the patient or user. As another example, the biological parameter may also comprise a characteristic which is detectable by image recognition, such as an iris and/or a geometry of a face of the patient or user.

Further, as outlined above, the handheld diagnostic device comprises at least one control unit configured for controlling the diagnostic measurement and for controlling the capturing of the image of the wound. Further, the control unit may be configured for performing at least one wound management process. The wound management process may comprise deriving at least one item of diagnostic information on the at least one wound of the patient which may be at least partially visible in the image. The wound management process may comprise at least one of:

- displaying the image of the wound on a display of the handheld diagnostic device;
- providing at least one measurement tool to a user, the measurement tool being configured for deriving the at least one item of diagnostic information from the image, specifically at least one measurement tool configured for determining a lateral extension of the wound;
- providing at least one image recognition tool configured for automatically deriving the at least one item of diagnostic information from the image, specifically at least one image analytical tool configured for determining a color information of the wound;
- providing at least one display tool for displaying at least one previous image of the wound;
- providing a download function for downloading patient information from at least one server device to the handheld diagnostic device;
- providing at least one graphics tool for displaying at least one temporal development of at least one diagnostic parameter related to the wound; and
- providing at least one method of escalation, specifically of communication, of the item of diagnostic information to a specialized health care professional.

Other options are feasible additionally or alternatively.

The term "wound management process" as used herein is a broad term and is to be given its ordinary and customary meaning to a person of ordinary skill in the art and is not to be limited to a special or customized meaning. The term specifically may refer, without limitation, to an arbitrary process of assisting a patient and/or healthcare professional with the treatment and/or the monitoring of at least one wound. Thus, as an example, the wound management process may comprise determining at least one item of diagnostic information of at least one wound of the patient. Specifically, the wound management process may include one or more steps of capturing and optionally recording at least one image of at least one wound of the patient and a subsequent examination of the captured image. The examination of the captured image may be performed automatically by appropriate software application, as will be outlined in more detail below. Further, the examination of the captured image may also be performed by a healthcare professional. The at least one step of the wound management process may further include an examination of a specific part of the patient's body, such as the feet, the legs or the arms of the patient, specifically by the healthcare professional. Further, the wound management process may include an examination of the whole body of the patient performed in two or more consecutive steps. Thus, in each step, an image of the wound of the patient may be captured and examined in order to determine at least one item of diagnostic information for every wound. Further, the user of the handheld diagnostic device may be guided through the wound management process by a software application, the software application may be configured for guiding the user step by step through the wound management process. Specifically, the software application may be configured for prompting the user to capture the at least one image of the wound in each of the at least one step of the wound management process.

Consequently, the term "item of diagnostic information" as used herein is a broad term and is to be given its ordinary and customary meaning to a person of ordinary skill in the art and is not to be limited to a special or customized meaning. The term specifically may refer, without limitation, to an arbitrary characteristic related to a health condition of a wound of the patient. For example, the item of diagnostic information may be suitable for making a medical diagnosis and for choosing an appropriate treatment of the wound. Further, the item of diagnostic information may also be suitable for following a healing process of the wound.

As outlined above, the control unit is configured for storing the at least one measurement result of the diagnostic measurement and the at least one image in the at least one database record of the patient. The control unit may further be configured for managing database records of a plurality of patients. The management of database records of a plurality of patients may include an identification of the patient and an assignment of the at least one measurement result of the diagnostic measurement and the at least one image to the electronic health record of the respective patient.

The handheld diagnostic device may further comprise at least one user management unit. The user management unit may be configured for limiting a use of at least part of the functionality of the handheld diagnostic device to at least one user group. The user group may be defined by at least one of: a list of users; a group of users fulfilling at least one predetermined clearance condition. Further, the user management unit may be configured for blocking the user of the handheld diagnostic device in case the user of the handheld diagnostic device may not be authenticated as a user having permission to use the handheld diagnostic device.

The term "user management unit" as used herein is a broad term and is to be given its ordinary and customary meaning to a person of ordinary skill in the art and is not to be limited to a special or customized meaning. The term specifically may refer, without limitation, to an arbitrary device which is configured for verifying the authentication of a user to use the handheld diagnostic device. The user management unit may fully or partially be embodied as a hardware unit. Alternatively, the user management unit may also fully or partially be embodied by software, such as a software running on the control unit, specifically a software running on a processor of the control unit.

Specifically, the user management unit may be configured for identifying the user of the handheld diagnostic device, for verifying the authentication of the user and further for limiting the use of at least a part of the functionality of the handheld diagnostic device to the respective user. For example, in case the user may be not allowed to perform the diagnostic measurement, the user management unit may prevent the user from performing the diagnostic measurement. As another example, in case the user may be not allowed to perform the wound management process, the handheld diagnostic device may prevent the user from performing the wound management process. In case the user may not be authenticated at all to use the handheld diagnostic device, the user management unit may be configured for blocking the use of the handheld diagnostic device to the user. Further, the authentication of a user may be verified based on a belonging of the user to at least one user group. The user group may be defined, as outlined above, by at least one of a list of users or a group of users fulfilling at least one predetermined clearance condition. Consequently, the term "predetermined clearance condition" as used herein is a broad term and is to be given its ordinary and customary meaning to a person of ordinary skill in the art and is not to be limited to a special or customized meaning. The term specifically may refer, without limitation, to a predetermined requirement that the user of the handheld diagnostic device must meet to be allowed to use the handheld diagnostic device. Specifically, the predetermined clearance condition may refer to a completion of a training course for a specific functionality of the handheld diagnostic device. For example, the training course may teach the user how to handle the handheld diagnostic device properly, such as for performing a diagnostic measurement and/or for performing the wound management process. Thus, information about the completion of the training course by a specific user may be stored on the data storage device of the handheld diagnostic device and additionally or alternatively on the server device.

Further, the handheld diagnostic device may comprise at least one data interface for exchanging unidirectionally or bidirectionally data with the at least one server device. The data interface may comprise at least one of a wireless or a wirebound interface. The data interface may be configured for communicating with at least one data management system. Specifically, the data management system may be or may comprise the hospital information system. Thus, the data interface may further be configured for communicating with the server device by using at least one secure data transmission. The secure data transmission may include an encryption of the transmitted data. Specifically, the encryption may ensure that only the receiving device, specifically the server device, is suitable for reading the transmitted data. For example, the secure data transmission may be realized by an end-to-end encryption.

The at least one control unit comprised by the handheld diagnostic device may further comprise at least one processor. The processor may be configured, specifically by software programming, for controlling the diagnostic measurement, for controlling the capturing of the image of the wound and for storing the at least one measurement result of the diagnostic measurement and the image in the at least one database record of the patient.

The term "processor" as generally used herein is a broad term and is to be given its ordinary and customary meaning to a person of ordinary skill in the art and is not to be limited to a special or customized meaning. The term specifically may refer, without limitation, to an arbitrary logic circuitry configured for performing basic operations of a computer or system, and/or, generally, to a device which is configured for performing calculations or logic operations. In particular, the processor may be configured for processing basic instructions that drive the computer or system. As an example, the processor may comprise at least one arithmetic logic unit (ALU), at least one floating-point unit (FPU), such as a math co-processor or a numeric coprocessor, a plurality of registers, specifically registers configured for supplying operands to the ALU and storing results of operations, and a memory, such as an L1 and L2 cache memory. In particular, the processor may be a multicore processor. Specifically, the processor may be or may comprise a central processing unit (CPU). Additionally or alternatively, the processor may be or may comprise a microprocessor, thus specifically the processor's elements may be contained in one single integrated circuitry (IC) chip. Additionally or alternatively, the processor may be or may comprise one or more application-specific integrated circuits (ASICs) and/or one or more fieldprogrammable gate arrays (FPGAs) or the like. The processor specifically may be configured, such as by software programming, for performing one or more evaluation operations.

In a further aspect of the disclosure, a diagnostic system is disclosed. The diagnostic system, specifically for point-of-care applications, comprises:

A. at least one handheld diagnostic device according to the present disclosure, such as according to any one of the embodiments disclosed above and/or according to any one of the embodiments disclosed in further detail below; and
B. at least one server device, the server device being configured for retrieving at least one measurement result of the diagnostic measurement and/or the at least one image of the at least one wound of the patient from the handheld diagnostic device.

The server device comprised by the diagnostic system may be part of the hospital information system. Further, the diagnostic system may comprise a plurality of the handheld diagnostic devices.

The term "system" as used herein is a broad term and is to be given its ordinary and customary meaning to a person of ordinary skill in the art and is not to be limited to a special or customized meaning. The term specifically may refer, without limitation, to an arbitrary set of interacting or interdependent components parts forming a whole. Specifically, the components may interact with each other in order to fulfill at least one common function. The at least two components may be handled independently or may be coupled or connectable. Thus, the term "diagnostic system" generally may refer to a group of at least two elements or components which are capable of interacting in order to perform at least one of: a diagnostic measurement; a wound management process. The diagnostic system may be an apparatus, specifically comprising at least two components, such as the at least one handheld diagnostic device and/or the at least one server device. For example, the diagnostic system may comprise at least one diagnostic measurement unit and at least one diagnostic test element for performing at least one diagnostic measurement. Additionally or alternatively, the diagnostic system may comprise at least one handheld diagnostic device which may be configured for performing the at least one wound management process, wherein the patient data retrieved from the handheld diagnostic device may be transmitted to the server device which is also comprised by the diagnostic system.

The term "patient data" as used herein is a broad term and is to be given its ordinary and customary meaning to a person of ordinary skill in the art and is not to be limited to a special or customized meaning. The term specifically may refer, without limitation, to any kind of patient-related information. Specifically, the patient data may be or may comprise at least one of: a measurement result of the diagnostic measurement; an image of the wound of the patient; an item of identification information; an item of diagnostic information. The patient data may be collected via at least one of: performing the at least one diagnostic measurement; capturing the at least one image of the wound of the patient; detecting the at least one identifier; performing the at least one wound management process; entering manually patient data into the electronic health record. The patient data may at least partially be stored on the storage device of the handheld diagnostic device. Further, the patient data may at least partially be stored on the server device, specifically in the hospital information system. More specifically, the patient data may be stored in the at least one database record of the patient, such as the electronic health record.

In a further aspect of the disclosure, a diagnostic method is disclosed. The method comprises the following steps which, as an example, may be performed in the given order. It shall be noted, however, that a different order is also possible. Further, it is also possible to perform one or more of the method steps once or repeatedly. Further, it is possible to perform two or more of the method steps simultaneously or in a timely overlapping fashion. The method may comprise further method steps which are not listed. The method comprises using at least one handheld diagnostic device according to the present disclosure, such as according to any one of the embodiments disclosed above and/or according to any one of the embodiments disclosed in further detail below.

The method further comprises:

i. performing at least one diagnostic measurement, the diagnostic measurement comprising using the diagnostic measurement unit and at least one diagnostic test element for determining at least one diagnostic parameter of at least one patient;
ii. capturing at least one image of at least one wound of the patient by using the camera of the handheld diagnostic device; and
iii. storing at least one measurement result of the diagnostic measurement and the at least one image in at least one database record of the patient.

The diagnostic measurement performed in step i. of the diagnostic method specifically may be or may comprise at least one in-vitro measurement. The term "in-vitro measurement" as used herein is a broad term and is to be given its ordinary and customary meaning to a person of ordinary skill in the art and is not to be limited to a special or customized meaning. The term specifically may refer, without limitation, to a way of performing a measurement outside the living organism. Specifically, the in-vitro measurement may use components of the living organism that have been isolated from the usual biological surroundings. For example, the diagnostic measurement may use a sample of a bodily fluid isolated from the patient and further applied to the diagnostic test element. Therefore, step i. of the diagnostic method may comprise applying at least one sample of a bodily fluid of the patient to the at least one diagnostic test element.

Further, steps i. and ii. of the diagnostic method may be performed, for one and the same patient, within a time span of no more than 15 minutes. The measurement result of the diagnostic measurement and the image may be combined. Thus, generally the performing of the at least one diagnostic measurement and the capturing of the at least one image of the at least one wound may correlate in time, allowing for correlating the results of both steps. Thus, as an example, a status of the wound may be linked or correlated to blood glucose measurement.

The diagnostic method may further comprise deriving at least one item of diagnostic information on the wound of the patient from the image. Further, the diagnostic method may comprise storing the at least one item of diagnostic information in the database record of the patient, specifically in the electronic health record of the patient.

In a further aspect of the disclosure, a computer program is disclosed, the computer program comprising instructions which, when the program is executed by the control unit of the handheld diagnostic device according to the present disclosure, such as according to any one of the embodiments disclosed above and/or according to any one of the embodiments disclosed in further detail below, cause the control unit to:

prompt a user to carry out a diagnostic measurement by using the diagnostic measurement unit and the diagnostic test element;
prompt the user to capture the at least one image of the at least one wound of the patient by using the camera; and
store at least one measurement result of the diagnostic measurement and the at least one image in the at least one database record of the patient.

Similarly, a computer-readable storage medium is disclosed, comprising instructions which, when executed by the control unit of the handheld diagnostic device according to the present disclosure, such as according to any one of the embodiments disclosed above and/or according to any one of the embodiments disclosed in further detail below, cause the control unit to:

prompt a user to carry out a diagnostic measurement by using the diagnostic measurement unit and the diagnostic test element;

prompt the user to capture the at least one image of the at least one wound of the patient by using the camera; and store at least one measurement result of the diagnostic measurement and the at least one image in the at least one database record of the patient.

In a further aspect of the present disclosure, a computer program is disclosed, comprising instructions which, when the program is executed by the diagnostic system according to the present disclosure, such as according to any one of the embodiments disclosed above and/or according to any one of the embodiments disclosed in further detail below, cause the server device of the diagnostic system to retrieve the patient data from the handheld diagnostic device, the patient data being generated by the diagnostic method according to the present disclosure, such as according to any one of the embodiments disclosed above and/or according to any one of the embodiments disclosed in further detail below, the patient data comprising the at least one measurement result of the diagnostic measurement and the at least one image of the at least one wound of the patient, and further cause the server device of the diagnostic system to store the patient data in at least one database record of the patient.

Similarly, a computer readable storage medium is disclosed, comprising instructions which, when executed by the diagnostic system according to the present disclosure, such as according to any one of the embodiments disclosed above and/or according to any one of the embodiments disclosed in further detail below, cause the server device of the diagnostic system to retrieve patient data from the handheld diagnostic device, the patient data being generated by the diagnostic method according to the present disclosure, such as according to any one of the embodiments disclosed above and/or according to any one of the embodiments disclosed in further detail below, the patient data comprising the at least one measurement result of the diagnostic measurement and the at least one image of the at least one wound of the patient, and further cause the server device of the diagnostic system to store the patient data in at least one database record of the patient.

As used herein, the term "computer-readable storage medium" specifically may refer to a non-transitory data storage means, such as a hardware storage medium having stored thereon computer-executable instructions. The computer-readable data carrier or storage medium specifically may be or may comprise a storage medium such as a random-access memory (RAM) and/or a read-only memory (ROM).

The computer program may also be embodied as a computer program product. As used herein, a computer program product may refer to the program as a tradable product. The product may generally exist in an arbitrary format, such as in a paper format, or on a computer-readable data carrier and/or on a computer-readable storage medium. Specifically, the computer program product may be distributed over a data network.

The methods and devices according to the present disclosure may provide a large number of advantages over similar methods and devices known in the art. Specifically, the method and devices as described herein may digitalize the above-mentioned workflow of the wound management process by executing it on a dedicated handheld diagnostic device for point-of-care applications. Thus, compared to methods and devices known in the art which provide smartphone-based wound management applications, the integration into the handheld diagnostic device for point-of-care applications may have significant impact, since the handheld diagnostic device may be already integrated into the regular and regulatory hospital workflow. For example, there may be rules for who has access to the handheld diagnostic device and what may be the procedure to clean and disinfect the handheld diagnostic device. Further, the integration of the wound management process into the handheld diagnostic device may avoid the use of a personal and/or additional mobile device. This may also include the synergic effect that the user of the handheld diagnostic device may only be registered once by the handheld diagnostic device in order to perform both tasks, the diagnostic measurement as well as the wound management process. Moreover, the patient's database record and the user database record of the user's organization may be already available as well as the camera of the handheld diagnostic device for capturing images of the wound of the patient.

In addition, the integration of the wound management process into handheld diagnostic devices approved and certificated for point-of-care applications may have significant advantages in comparison to the use of generic mobile devices for such wound management processes. Such dedicated point-of-care handheld diagnostic devices fulfill the much higher requirements regarding both cleaning and disinfection as well as robustness of the devices which are also relevant for wound management processes which take place in the same surroundings.

The workflow of the wound management process including capturing the at least one image may be implemented in an application that guides the user through the needed steps, thus reducing his or her mental load. The handheld diagnostic device may communicate the patient data, such as the at least one measurement result and the at least one image via the data interfaces to the hospital information system or any other specified gateway to the electronic health record. Significant synergic effect can be gained from the fact the handheld diagnostic device may already be tasked with fulfilling and securing the specific information technology and cyber security requirements and configurations.

Moreover, by adding the application for performing the wound management process to the handheld diagnostic device that is configured for performing at least one diagnostic measurement may use the synergy with glucose management for the patient suffering from diabetes. Thus, the handheld diagnostic device may provide a user-friendly diagnostic measurement, such as a blood glucose measurement, and a user-friendly wound management process, by combining both features in one and the same device. Further, the method and devices as described herein may allow for a correlation of the patient data with each other, such as the at least one measurement result of the diagnostic measurement and the at least one captured image of the wound of the patient, which may also open up synergies in the medical treatment of the patient.

Summarizing and without excluding further possible embodiments, the following embodiments may be envisaged:

Embodiment 1: A handheld diagnostic device, specifically for point-of-care applications, comprising:

a. at least one diagnostic measurement unit configured for performing at least one diagnostic measurement, the diagnostic measurement unit comprising at least one test element port for determining at least one diagnostic parameter of at least one patient by using at least one diagnostic test element;

b. at least one camera configured for capturing at least one image of at least one wound of the patient, specifically of the same patient as in a.; and c. at least one control unit, the control unit being configured for controlling the diagnostic measurement and for controlling the capturing of the image of the wound, wherein the control unit is further configured for storing at least one measurement result of the diagnostic measurement and the at least one image in at least one database record of the patient.

Embodiment 2: The handheld diagnostic device according to the preceding embodiment, wherein the database record contains at least one item of identification information identifying the patient, the at least one image and the at least one measurement result.

Embodiment 3: The handheld diagnostic device according to any one of the preceding embodiments, wherein the database record is at least partially stored on the handheld diagnostic device, specifically in at least one data storage device of the handheld diagnostic device.

Embodiment 4: The handheld diagnostic device according to any one of the preceding embodiments, wherein the database record is at least partially stored on at least one server device, specifically in a hospital information system, wherein the handheld diagnostic device is configured for electronically communicating with the server device, specifically with the hospital information system.

Embodiment 5: The handheld diagnostic device according to any one of the preceding embodiments, wherein the database record of the patient is at least partially comprised by an electronic health record stored in a hospital information system.

Embodiment 6: The handheld diagnostic device according to the preceding embodiment, wherein the control unit is configured for assigning the measurement result and the image to at least one patient's electronic health record.

Embodiment 7: The handheld diagnostic device according to any one of the preceding embodiments, wherein the handheld diagnostic device comprises at least one energy storage device for providing electrical energy to at least one of the diagnostic measurement unit, the camera and the control unit.

Embodiment 8: The handheld diagnostic device according to any one of the preceding embodiments, wherein the handheld diagnostic device is a wireless handheld diagnostic device.

Embodiment 9: The handheld diagnostic device according to any one of the preceding embodiments, wherein the handheld diagnostic device has a volume of less than 0.001 $m^3$.

Embodiment 10: The handheld diagnostic device according to any one of the preceding embodiments, wherein the handheld diagnostic device has a weight of less than 1 kg.

Embodiment 11: The handheld diagnostic device according to any one of the preceding embodiments, wherein the handheld diagnostic device comprises at least one display and at least one user interface.

Embodiment 12: The handheld diagnostic device according to any one of the preceding embodiments, wherein the diagnostic parameter comprises at least one parameter selected from the group consisting of: a glucose concentration in at least one body fluid of the patient, specifically a blood glucose value; a coagulation parameter of the patient; a ketone concentration in at least one body fluid of the patient; a lactate concentration in at least one body fluid of the patient.

Embodiment 13: The handheld diagnostic device according to any one of the preceding embodiments, wherein the diagnostic test element comprises at least one of an electrochemical test element and an optical test element.

Embodiment 14: The handheld diagnostic device according to any one of the preceding embodiments, wherein the test element comprises at least one test strip, wherein the test element port comprises at least one test strip port.

Embodiment 15: The handheld diagnostic device according to any one of the preceding embodiments, wherein the handheld diagnostic device is further configured for identifying at least one of the patient or a user of the handheld diagnostic device.

Embodiment 16: The handheld diagnostic device according to the preceding embodiment, wherein the handheld diagnostic device is configured for detecting at least one identifier, the identifier identifying the patient or user, respectively.

Embodiment 17: The handheld diagnostic device according to the preceding embodiment, wherein the identifier comprises at least one identifier selected from the group consisting of: an optical identifier, specifically at least one of a bar code or a QR code; an electronic identifier, specifically an RFID tag and/or an NFC tag.

Embodiment 18: The handheld diagnostic device according to any one of the three preceding embodiments, wherein the handheld diagnostic device is configured for identifying the patient or user, respectively, by using image recognition, specifically by using face recognition.

Embodiment 19: The handheld diagnostic device according to any one of the four preceding embodiments, wherein the handheld diagnostic device further comprises at least one biometric sensor configured for identifying the patient by determining at least one biometric parameter of the patient or user, respectively.

Embodiment 20: The handheld diagnostic device according to any one of the preceding embodiments, wherein the control unit is further configured for performing at least one wound management process, wherein the wound management process comprises deriving at least one item of diagnostic information on the at least one wound of the patient which is at least partially visible in the image.

Embodiment 21: The handheld diagnostic device according to the preceding embodiment, wherein the wound management process comprises at least one of:

displaying the image of the wound on a display of the handheld diagnostic device;

providing at least one measurement tool to a user, the measurement tool being configured for deriving the at least one item of diagnostic information from the image, specifically at least one measurement tool configured for determining a lateral extension of the wound;

providing at least one image recognition tool configured for automatically deriving the at least one item of diagnostic information from the image, specifically at least one image analytical tool configured for determining a color information of the wound;

providing at least one display tool for displaying at least one previous image of the wound;

providing a download function for downloading patient information from at least one server device to the handheld diagnostic device;

providing at least one graphics tool for displaying at least one temporal development of at least one diagnostic parameter related to the wound; and providing at least one method of escalation of the item of diagnostic information to a specialized health care professional.

Embodiment 22: The handheld diagnostic device according to any one of the preceding embodiments, wherein the control unit is configured for managing database records of a plurality of patients.

Embodiment 23: The handheld diagnostic device according to any one of the preceding embodiments, further comprising at least one user management unit, wherein the user management unit is configured for limiting a use of at least part of the functionality of the handheld diagnostic device to at least one user group.

Embodiment 24: The handheld diagnostic device according to the preceding embodiment, wherein the user group is defined by at least one of: a list of users; a group of users fulfilling at least one predetermined clearance condition.

Embodiment 25: The handheld diagnostic device according to any one of the two preceding embodiments, wherein the user management unit is configured for blocking the use of the handheld diagnostic device in case the user of the handheld diagnostic devices is not authenticated as a user having permission to use the handheld diagnostic device.

Embodiment 26: The handheld diagnostic device according to any one of the preceding embodiments, further comprising at least one data interface for exchanging data with at least one server device.

Embodiment 27: The handheld diagnostic device according to the preceding embodiment, wherein the data interface is configured for communicating with at least one data management system.

Embodiment 28: The handheld diagnostic device according to any one of the two preceding embodiments, wherein the data interface is configured for communicating with the server device by using at least one secure data transmission.

Embodiment 29: The handheld diagnostic device according to any one of the preceding embodiments, wherein the control unit comprises at least one processor, the processor being configured by software programming for controlling the diagnostic measurement, for controlling the capturing of the image of the wound and for storing the at least one measurement result of the diagnostic measurement and the image in at least one database record of the patient.

Embodiment 30: A diagnostic system, specifically for point-of-care applications, comprising:

A. at least one handheld diagnostic device according to any one of the embodiments 1 to 29; and B. at least one server device, the server device being configured for retrieving at least one measurement result of the diagnostic measurement and/or the at least one image of the at least one wound of the patient from the handheld diagnostic device.

Embodiment 31: The diagnostic system according to the preceding embodiment, wherein the server device is part of a hospital information system.

Embodiment 32: The diagnostic system according to any one of the preceding embodiments referring to a diagnostic system, wherein the diagnostic system comprises a plurality of the handheld diagnostic devices.

Embodiment 33: A diagnostic method, specifically for point-of-care applications, the diagnostic method comprising using at least one handheld diagnostic device according to any one of the embodiments 1 to 29 referring to a handheld diagnostic device, the method comprising:

i. performing at least one diagnostic measurement, the diagnostic measurement comprising using the diagnostic measurement unit and at least one diagnostic test element for determining at least one diagnostic parameter of at least one patient;

ii. capturing at least one image of at least one wound of the patient by using the camera of the handheld diagnostic device; and iii. storing at least one measurement result of the diagnostic measurement and the at least one image in at least one database record of the patient.

Embodiment 34: The method according to the preceding embodiment, wherein the diagnostic measurement in step i. is an in-vitro measurement.

Embodiment 35: The method according to any one of the preceding method embodiments, wherein step i. comprises applying at least one sample of a bodily fluid of the patient to the at least one diagnostic test element.

Embodiment 36: The method according to any one of the preceding method embodiments, wherein steps i. and ii. are performed, for one and the same patient, within a time span of no more than 15 minutes.

Embodiment 37: The method according to any one of the preceding method embodiments, wherein the measurement result of the diagnostic measurement and the image are combined.

Embodiment 38: The method according to any one of the preceding method embodiments, wherein the method further comprises deriving at least one item of diagnostic information on the wound of the patient from the image.

Embodiment 39: The method according to the preceding embodiment, wherein the method further comprises storing the at least one item of diagnostic information in the database record of the patient.

Embodiment 40: A computer program comprising instructions which, when the program is executed by the control unit of the handheld diagnostic device according to any one of the embodiments 1 to 29, cause the control unit to prompt a user to carry out a diagnostic measurement by using the diagnostic measurement unit and the diagnostic test element;

prompt the user to capture the at least one image of the at least one wound of the patient by using the camera; and store at least one measurement result of the diagnostic measurement and the at least one image in the at least one database record of the patient.

Embodiment 41: A computer-readable storage medium comprising instructions which, when executed by the control unit of the handheld diagnostic device according to any one of the embodiments 1 to 29, cause the control unit to prompt a user to carry out a diagnostic measurement by using the diagnostic measurement unit and the diagnostic test element;

prompt the user to capture the at least one image of the at least one wound of the patient by using the camera; and store at least one measurement result of the diagnostic measurement and the at least one image in the at least one database record of the patient.

Embodiment 42: A computer program comprising instructions which, when the program is executed by the diagnostic system according to any one of the embodiments 30 to 32, cause the server device of the diagnostic system to retrieve patient data from the handheld diagnostic device, the patient data being generated by the diagnostic method according to any one of the embodiments 33 to 39, the patient data comprising the at least one measurement result of the diagnostic measurement and the at least one image of the at least one wound of the patient, and further cause the server device of the diagnostic system to store the patient data in at least one database record of the patient.

Embodiment 43: computer-readable storage medium comprising instructions which, when executed by the diagnostic system according to any one of the embodiments 30 to 32, cause the server device of the diagnostic system to retrieve patient data from the handheld diagnostic device, the patient data being generated by the diagnostic method according to any one of the embodiments 33 to 39, the patient data comprising the at least one measurement result of the diagnostic measurement and the at least one image of the at least one wound of the patient, and further cause the server device of the diagnostic system to store the patient data in at least one database record of the patient.

In order that the embodiments of the present disclosure may be more readily understood, reference is made to the following examples, which are intended to illustrate the disclosure, but not limit the scope thereof.

In FIG. 1, embodiments of a diagnostic system 110, a handheld diagnostic device 112 and a diagnostic test element 114, respectively, are shown in a schematic view. The diagnostic system 110 comprises the at least one handheld diagnostic device 112 and at least one server device 116. The handheld diagnostic device 112 comprises at least one diagnostic measurement unit 118, at least one camera 120 and at least one control unit 122.

The at least one diagnostic measurement unit 118 comprises at least one test element port 124 for determining at least one diagnostic parameter of at least one patient using the at least one diagnostic test element 114. The test element port 124 may be configured for receiving the at least one diagnostic test element 114. The diagnostic test element 114 may also form part of the diagnostic system 110. For example, the diagnostic test element 114 may be embodied as a test strip 126. The diagnostic test element 114 may comprise at least one of an electrochemical test element and/or an optical test element, wherein the electrochemical and/or optical test element may be configured for changing an electrochemically and/or optically detectable property in the presence of the diagnostic parameter. Thus, the diagnostic test element 114 may be configured for detecting the at least one diagnostic parameter in a sample of bodily fluid of the patient, for example in a sample of blood, interstitial fluid, urine, *salvia* or other types of body fluids. The handheld diagnostic device 112 may further comprise at least one display 128 and/or at least one user interface for displaying the result of the diagnostic measurement to a user and for interacting with the user of the handheld diagnostic device 112.

Further, the handheld diagnostic device 112 comprises the at least one camera 120 configured for capturing at least one image of at least one wound 130 of the patient, for example a wound 130 located at the patient's foot 131.

The handheld diagnostic device 112 and/or the camera 120 of the handheld diagnostic device 112 may further be configured for detecting at least one identifier 133, the identifier 133 identifying the patient or user. The identifier may comprise an optical identifier, such as a barcode or a QR code, and/or an electronic identifier, such as an RFID tag and/or an NFC tag. Thus, as an example, the identifier 133 may be comprised by a badge and/or a bracelet of the user, such as a healthcare professional, and the user may scan the identifier 133 of the badge and/or the bracelet by using the handheld diagnostic device 112. Additionally or alternatively, the identifier 133 may be comprised by a wristband of the patient, and the user may scan the identifier 133 of the wristband by using the handheld diagnostic device 112. Other options are feasible. The handheld diagnostic device 112 may comprise an appropriate reading device configured for detecting the identifier 133, such as the electronic identifier. The handheld diagnostic device 112 may also be configured for identifying the patient or user by image recognition, specifically by face recognition. Further, the handheld diagnostic device 112 may also comprise a biometric sensor configured for identifying the patient and/or the user by determining at least one biometric parameter, such as a fingerprint and/or an iris of the patient or user, respectively. Thus, the camera 120 of the handheld diagnostic device 112 may also be used as the biometric sensor, wherein the camera 120 may be used for capturing an image of the patient or user to image a specific characteristic, such as a face and/or an iris, and which may further be used to identify the patient or user, respectively.

The handheld diagnostic device 112 comprises the at least one control unit 122 configured for controlling the at least one diagnostic measurement and for controlling the capturing of the at least one image of the wound 130 of the patient. The control unit 122 may further be configured for performing at least one wound management process, wherein the wound management process may comprise deriving at least one item of diagnostic information on the wound 130 of the patient.

The control unit 122 is further configured for storing the at least one measurement result of the diagnostic measurement and the at least one image of the wound 130 in at least one database record of the patient. The database record may contain at least one item of identification of the patient, such as a name, a date of birth, an identification number, and further the at least one image of the wound 130, the at least one measurement result and the at least one item of diagnostic information. The database record may at least partially be stored on the handheld diagnostic device 112, specifically in at least one data storage device 132 of the handheld diagnostic device 112. The database record may also at least partially be stored on the at least one server device 116, specifically in a hospital information system 134. Thus, the handheld diagnostic device 112 may be configured for electronically communicating with the hospital information system 134.

Further, the diagnostic system 110 may comprise at least one data interface 136 for exchanging unidirectionally or bidirectionally data with the at least one server device 116. The server device 116 specifically, may be configured for retrieving at least one measurement result of the diagnostic measurement and/or the at least one image of the at least one wound 130 of the patient, also referred to as patient data, from the handheld diagnostic device 112. Specifically, the data interface 136 may be configured for exchanging data, such as patient data, and/or commands with the handheld diagnostic device 112. Specifically, the patient data may comprise at least one of: an item of identification of the patient; an image of the wound 130; a measurement result of the diagnostic measurement; an item of diagnostic information. The data interface 136 may further be configured for communicating by using at least one secure data transmission.

Further, the at least one server device 116 of the diagnostic system may be embodied as a cloud server 138. Therefore, the server device 116 may be configured for communicating with a plurality of handheld diagnostic devices 112. Thus, the hospital information system 134 may comprise a plurality of database records on a plurality of patients containing the patient data of the respective patient. The database record of a single patient may be at least partially comprised by an electronic health record 140. The electronic health record 140 may be or may comprise an electronic medical file of the patient and, thus, may comprise patient-related information, such as the name, the age and the gender of the patient, and health information about present and/or past diseases as well as medical treatments of the patient. Further, the control unit 122 of the handheld diagnostic device 112 may be configured for assigning the patient data recorded by the handheld diagnostic device 112 to the at least one's electronic health record 140 of this patient.

The handheld diagnostic device 112 may further comprise at least one processor 142. The processor 142 may be configured, specifically by software programming, for controlling the diagnostic measurement, for controlling the capturing of the image of the wound 130 and for storing the at least one measurement result of the diagnostic measurement and the image captured by the handheld diagnostic device 112 in the at least one database record of the patient. The processor 142 may also be configured, specifically by software programming, for controlling the wound management process and for storing the item of diagnostic information.

Figure 2:
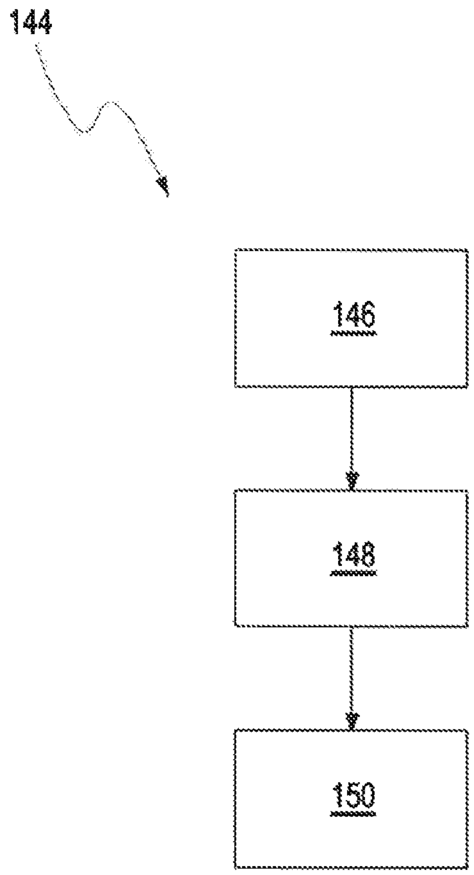
FIG. 2 shows a flow chart of an embodiment of a diagnostic method in accordance with an embodiment of the present disclosure.

The diagnostic system 110 is configured, specifically by software programming, for performing a diagnostic method, specifically for point-of-care applications. In FIG. 2, a flow chart of an exemplary embodiment of the method is shown, wherein the method is denoted by reference number 144. The diagnostic method 144 comprises using the at least one handheld diagnostic device 112. The diagnostic method 144 comprises the following steps, which may specifically be performed in the given order. Still, a different order may also be possible. It may be possible to perform two or more of the method steps fully or partially simultaneously. It may further be possible to perform one, more than one or even all of the method steps once or repeatedly. The diagnostic method 144 may comprise additional method steps that are not listed.

The diagnostic method 144 comprises the following steps:

i. (denoted with reference number 146) performing at least one diagnostic measurement, the diagnostic measurement comprising using the diagnostic measurement unit 118 and the at least one diagnostic test element 114 for determining the at least one diagnostic parameter of the at least one patient;

ii. (denoted with reference number 148) capturing the at least one image of the at least one wound 130 of the patient by using the camera 120 of the handheld diagnostic device 112; and iii. (denoted with reference number 150) storing the at least one measurement result of the diagnostic measurement and the at least one image in the at least one database record of the patient.

As outlined above, the diagnostic method 144 comprises using the at least one diagnostic handheld device 112. The usage of the handheld diagnostic device 112 may be controlled by a user management unit, the user management unit may be configured for limiting the use of at least part of the functionality of the handheld diagnostic device 112 to at least one user group. The user group may be defined by at least one of: a list of users; a group of users fulfilling at least on predetermined clearance condition. The predetermined clearance condition may refer to a completion of a training course, for example the training course may teach the user how to handle the handheld diagnostic device 112 properly. The usage of the handheld diagnostic device 112 may further be restricted to a predetermined list of user, wherein the users may be allowed to use a specific functionality of the handheld diagnostic device 112. In case the user of the handheld diagnostic device 112 is not authenticated to use the handheld diagnostic device 112, the user management unit may be configured for blocking the use of the handheld diagnostic device 112. The allowance of a user to use the handheld diagnostic device 112 may be checked in advanced of each method step of the diagnostic method 144, specifically in advance of steps i. and ii.

Step i. of the diagnostic method 144 may comprise applying at least one sample of the bodily fluid of the patient to the at least one diagnostic test element 114. Thus, the diagnostic measurement may be an in vitro measurement. The diagnostic system 110, specifically the control unit 122 of the handheld diagnostic device 112, may be configured, specifically by executing a computer program, for prompting a user to assist in carrying out the diagnostic measurement. The prompting, as an example, may take place by visually displaying instructions, for example on the display 128 of the handheld diagnostic device 112.

In step ii. of the diagnostic method 144, at least one image of the wound 130 of the patient is captured. The control unit 122 may also be configured, specifically by executing the computer program, for prompting the user to assist in capturing the at least one image of the wound 130 of the patient. The image, in which the wound 130 of the patient may be at least partially visible, may be used for the wound management process. The wound management process may comprise deriving at least one item of diagnostic information on the wound 130 of the patient. The wound management process may provide tools for an automatic examination of the wound 130, such as at least one measurement tool, at least one image recognition tool, at least one display tool, at least one download function and/or at least one graphics tool. The at least one item of diagnostic information derived from the wound management process may form part of the patient data and thus, may be stored in the patient's electronic health record. Further, steps i. and ii. may be performed, for one and the same patient, within a time span of no more than 15 minutes.

Further, the diagnostic method 144 may be at least partially computer implemented, specifically step iii. of the diagnostic method 144. The control unit 122 of the handheld diagnostic device 112 may be configured to execute the computer program which may cause the control unit 122 to store the at least one measurement result of the diagnostic measurement and the at least one image in the at least one database record of the patient. As outlined above, for the method steps which are not computer-implemented, the control unit 122 may be configured to prompt the user to assist in performing steps i. and ii. Further, the server device 116 may be configured, specifically by software programming, to retrieve the patient data, such as the measurement result of the diagnostic measurement and the at least one image of the wound 130 of the at least one patient, from the handheld diagnostic device 112. Specifically, the patient data may be retrieved by the server device 116 from the data storage device 132 of the handheld diagnostic device 112.

Figure 3:
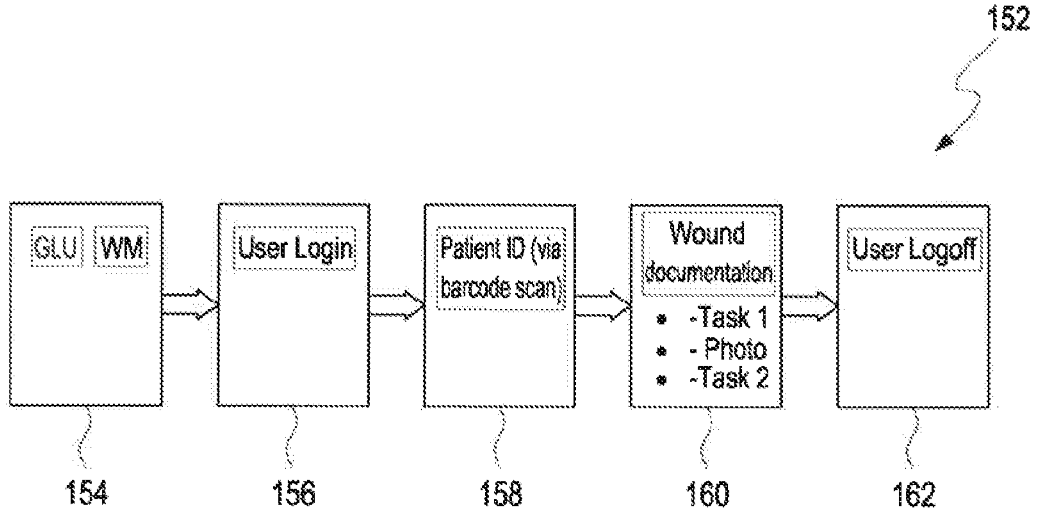
FIG. 3 shows a flow chart of an embodiment of a (non-integrated) wound management workflow in accordance with an embodiment of the present disclosure.

In FIG. 3, a flow chart of an exemplary embodiment of a wound management workflow 152 is shown. The wound management workflow 152 may comprise using the at least one handheld diagnostic device 112. Specifically, the wound management workflow 152 may be performed by using a software application running on the at least one handheld diagnostic device 152. The software application may guide the user of the handheld diagnostic device 112 through the wound management workflow 152. For example, the software application may be configured for prompting the user of the handheld diagnostic device 112 to perform the wound management workflow 152. In order to initiate the wound management workflow 152, the user may have to select the appropriate functionality 154 of the handheld diagnostic device 112, for example by starting the software application configured for performing the wound management (WM) workflow 152 via the user interface of the handheld diagnostic device 112. In a first step of the wound management workflow 152, the handheld diagnostic device 112 may perform a user login 156. Specifically, the handheld diagnostic device 112 may identify the user, for example by reading the at least one identifier 133 of the user and/or by using image recognition, such as face recognition. Further, if the user may be identified by the handheld diagnostic device 112, the handheld diagnostic device may verify the authentication of the user to use the specific functionality of the handheld diagnostic device 112. In a further step of the wound management workflow, the patient may be identified 158 by the handheld diagnostic device 112. For example, the handheld diagnostic device 112 may identify the patient 158 by reading the at least one identifier 133 of the patient. The user may assist the handheld diagnostic device 112 in reading the identifier 133 of the patient, such as by scanning the badge, the bracelet and/or wristband comprising the at least one identifier 133 of the patient. Further, the wound management workflow 152 may comprise the wound management process 160. The wound management process 160 may comprise capturing the at least one image of at least one wound 130 of the patient. Thus, the software application running on the handheld diagnostic device 112 may prompt the user to identify the wounds 130 of the patient and to capture at least one image for each wound 130 of the patient. In case the user completed the wound management process 160, the wound management workflow 152 may end by logging off the user 162 from the handheld diagnostic device 112.

Figure 4:
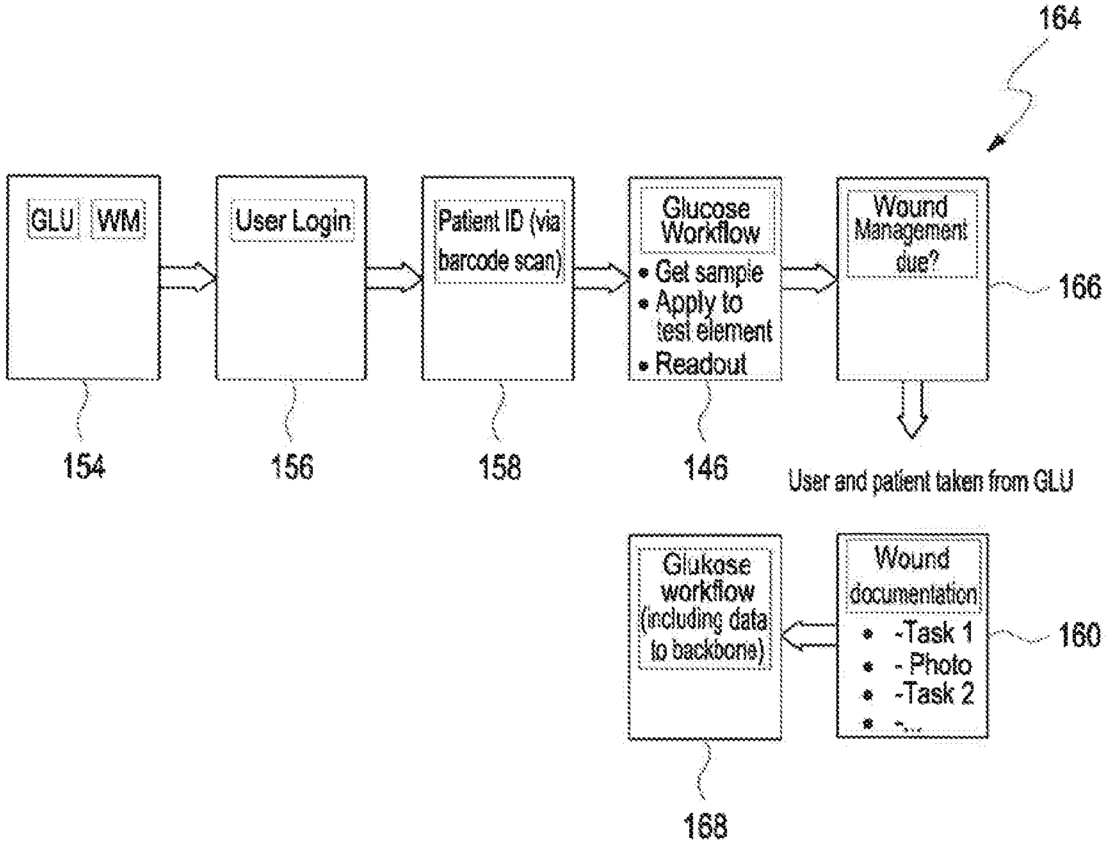
FIG. 4 shows a flow chart of an embodiment of an integrated workflow in accordance with an embodiment of the present disclosure.

In FIG. 4, a flow chart of an exemplary embodiment of an integrated workflow 164 is shown. For example, the wound management workflow 152 may be integrated into the performance of at least one diagnostic measurement 146. Similar to the wound management workflow 152, described in detail above, the integrated workflow 164 may comprise using the at least one handheld diagnostic device 112. Further, the integrated workflow 164 may also be performed by using a software application running on the handheld diagnostic device 112. The first three steps of the integrated workflow may be similar to the wound management workflow 152, therefore reference is made to the description of FIG. 3. The steps may be: starting the software application configured for performing the integrated workflow 164 by selecting the appropriate functionality 154, logging in of the user 156 and identifying the patient 158. A further step of the integrated workflow may comprise performing at least one diagnostic measurement 146. This step may be similar to method step i) and thus, reference is made to the description of the diagnostic method 144, shown in FIG. 2. In a further step of the integrated workflow 164, the software application may be configured for querying 166 whether a wound management process 160 is due for the respective patient. The software application may query the electronic health record 140 of the patient. Additionally or alternatively, the software application may query the user of the handheld diagnostic device 112 if the wound management process 160 is due. In one embodiment, the wound management process may be due in specific intervals, e.g., once per day. If the wound management process 160 is due, the software application may be configured for at least one of: prompting the user of the handheld diagnostic device 112 to perform the wound management process 160; taking the patient data and the user data from the diagnostic measurement to start the wound management process 160. Further, the integrated workflow 164 may comprise exchanging the recorded data 168, such as the diagnostic measurement result and the at least one image of the wound 130 of the patient, with the at least one server device 116.

LIST OF REFERENCE NUMBERS

110 diagnostic system
112 handheld diagnostic device
114 diagnostic test element
116 server device
118 diagnostic measurement unit
120 camera
122 control unit
124 test element port
126 test strip
128 display
130 wound
131 patient's foot
132 data storage device of the handheld diagnostic device
133 identifier
134 hospital information system
136 data interface
138 cloud server
140 electronic health record
142 processor
144 diagnostic method
146 performing at least one diagnostic measurement (step i.)
148 capturing at least one image (step ii.)
150 storing the at least one measurement result of the diagnostic measurement and the at least one image (step iii.)
152 wound management workflow
154 selecting a functionality of the handheld diagnostic device
156 user login
158 identifying the patient
160 wound management process
162 user logoff
164 integrated workflow
166 querying if the wound management is due
168 exchanging data

What is claimed is:

1. A handheld diagnostic device comprising:

a. a housing;

b. at least one diagnostic measurement unit disposed within the housing, and performing at least one diagnostic measurement, the diagnostic measurement unit comprising:

(i) at least one test element port for receiving a test element comprising at least one reagent that changes a detectable property in the presence of at least one of a coagulation parameter, glucose, lactate, and ketone and (ii) at least one testing device for electrochemical testing and/or optical testing of a sample using the test element;

c. at least one camera disposed within the housing and capturing at least one image of at least one wound of a patient; and d. at least one control unit disposed within the housing, the control unit (i) controlling the diagnostic measurement unit to perform testing of the sample using the test element, when received within the test element port, to obtain at least one diagnostic measurement result indicative of the presence of at least one of the coagulation parameter, glucose, lactate, and ketone in a sample from the patient, (ii) controlling the camera to capture the at least one image of the at least one wound, and (iii) storing the at least one diagnostic measurement result and the at least one image in at least one database record of the patient.

2. The handheld diagnostic device according to claim 1, wherein the at least one database record contains at least one item of identification information identifying the patient, the at least one image and the at least one measurement result.

3. The handheld diagnostic device according to claim 1, wherein the at least one database record is at least partially stored on at least one server device, wherein the handheld diagnostic device is in electronic communication with the server device.

4. The handheld diagnostic device according to claim 1, wherein the at least one database record of the patient is at least partially comprised by an electronic health record stored in a hospital information system and wherein the control unit assigns the measurement result and the image to at least one patient's electronic health record.

5. The handheld diagnostic device according to claim 1, and comprising an electrochemical test element.

6. The handheld diagnostic device according to claim 1, wherein the handheld diagnostic device identifies at least one of the patient or a user of the handheld diagnostic device.

7. The handheld diagnostic device according to claim 1, wherein the control unit further performs at least one wound management process, wherein the wound management process comprises deriving at least one item of diagnostic information on the at least one wound of the patient which is at least partially visible in the image.

8. The handheld diagnostic device according to claim 7, wherein the wound management process comprises at least one of:

displaying the image of the wound on a display of the handheld diagnostic device;

providing at least one measurement tool to a user, the measurement tool being configured for deriving the at least one item of diagnostic information from the image;

providing at least one image recognition tool configured for automatically deriving the at least one item of diagnostic information from the image;

providing at least one display tool for displaying at least one previous image of the wound;

providing a download function for downloading patient information from at least one server device to the handheld diagnostic device;

providing at least one graphics tool for displaying at least one temporal development of at least one diagnostic parameter related to the wound; and providing at least one method of escalation of the item of diagnostic information to a health care professional.

9. The handheld diagnostic device according to claim 1, further comprising at least one user management unit disposed within the housing, wherein the user management unit is configured for limiting a use of at least part of the functionality of the handheld diagnostic device to at least one user group and/or wherein the user management unit is configured for blocking the use of the handheld diagnostic device in case the user of the handheld diagnostic device is not authenticated as a user having permission to use the handheld diagnostic device.

10. The handheld diagnostic device according to claim 1, wherein the handheld diagnostic device is configured for point-of-care applications, wherein the point-of-care application is an application in a professional healthcare facility, wherein the point-of-care application is performed by a professional healthcare provider at or near to the patient.

11. The handheld diagnostic device according to claim 1, further comprising at least one user management unit disposed within the housing, wherein the user management unit limits a use of at least part of the functionality of the handheld diagnostic device to at least one user group.

12. The handheld diagnostic device according to claim 11, wherein the user management unit blocks the use of the handheld diagnostic device in case the user of the handheld diagnostic device is not authenticated as a user having permission to use the handheld diagnostic device.

13. A diagnostic system comprising:

A. at least one handheld diagnostic device, the handheld diagnostic device comprising:

a. a housing:

b. at least one diagnostic measurement unit disposed within the housing and performing at least one diagnostic measurement, the diagnostic measurement unit comprising (i) at least one test element port for receiving a test element comprising at least one reagent that changes a detectable property in the presence of at least one of a coagulation parameter, glucose, lactate, and ketone and (ii) at least one testing device for electrochemical testing and/or optical testing of a sample using the test element:

c. at least one camera disposed within the housing and capturing at least one image of at least one wound of a patient; and d. at least one control unit disposed within the housing, the control unit (i) controlling the diagnostic measurement unit to perform testing of a sample using the test element, when received within the test element port, to obtain at least one diagnostic measurement result indicative of the presence of at least one of the coagulation parameter, glucose, lactate, and ketone in a sample from the patient, (ii) controlling the camera to capture an image of the wound, and (iii) storing the at least one diagnostic measurement result and the at least one image in at least one database record of the patient; and B. at least one server device, the server device being configured for retrieving at least one measurement result of the diagnostic measurement and/or the at least one image of the at least one wound of the patient from the handheld diagnostic device.

14. A diagnostic method, the diagnostic method comprising:

i. providing a handheld diagnostic device comprising:

a. a housing;

b. at least one diagnostic measurement unit disposed within the housing and performing at least one diagnostic measurement, the diagnostic measurement unit comprising (i) at least one test element port for receiving a test element comprising at least one reagent that changes a detectable property in the presence of at least one of a coagulation parameter, glucose, lactate, and ketone and (ii) at least one testing device for electrochemical testing and/or optical testing of a sample using the test element;

c. at least one camera disposed within the housing and capturing at least one image of at least one wound of a patient; and d. at least one control unit disposed within the housing, the control unit (i) controlling the diagnostic measurement unit to perform testing of a sample using the test element, when received within the test element port, to obtain at least one diagnostic measurement result indicative of the presence of at least one of the coagulation parameter, glucose, lactate, and the ketone in a sample from the patient, (ii) controlling the camera to capture an image of the wound, and (iii) storing the at least one diagnostic measurement result and the at least one image in at least one database record of the patient;

ii. performing at least one diagnostic measurement to obtain at least one diagnostic measurement indicative of the presence of at least one of a coagulation parameter, glucose, lactate, and a ketone in a patient sample applied to the test element, the diagnostic measurement comprising using the diagnostic measurement unit and at least one diagnostic test element for determining at least one diagnostic parameter of at least one patient;

iii. operating the camera to capture the at least one image of the at least one wound of the patient; and iv. storing at least one measurement result of the diagnostic measurement and the at least one image in the at least one database record of the patient.

15. The handheld diagnostic device according to claim 1, wherein the diagnostic measurement unit has a test element received in the test element port, the control unit controls the diagnostic measurement unit to conduct a diagnostic measurement, and obtains a diagnostic measurement result comprising a diagnostic parameter, and the electronic control unit stores the diagnostic parameter.

16. The handheld diagnostic device according to claim 15, wherein the diagnostic measurement unit comprises at least one test element.

17. The handheld diagnostic device according to claim 1, wherein the control unit further performs at least one wound management process, wherein the wound management process comprises deriving at least one item of diagnostic information on the at least one wound of the patient which is at least partially visible in the image.

* * * * *